United States Patent
Ippoliti

(10) Patent No.: US 6,211,374 B1
(45) Date of Patent: Apr. 3, 2001

(54) WATER SOLUBLE, PYRAN-BASED PHOTOCHROMIC COMPOUNDS HAVING CARBOXYLATE FUNCTIONALITY

(76) Inventor: Joseph Thomas Ippoliti, 641 Ashland Ave., St. Paul, MN (US) 55104

(*) Notice: Subject to any disclaimer, the term of this patent is extended or adjusted under 35 U.S.C. 154(b) by 0 days.

(21) Appl. No.: 09/064,974

(22) Filed: Apr. 22, 1998

Related U.S. Application Data

(60) Provisional application No. 60/044,149, filed on Apr. 23, 1997.

(51) Int. Cl.$^7$ .................... C07D 215/60; C07D 215/10; C07D 215/20; C07D 405/00; C07D 311/92
(52) U.S. Cl. .................... 546/153; 546/155; 546/156; 546/196; 546/269; 546/282.7; 548/525; 549/60; 549/389
(58) Field of Search .................... 549/60, 389; 546/153, 546/155, 156, 196, 269, 282.7; 548/525

(56) References Cited

U.S. PATENT DOCUMENTS

| | | | |
|---|---|---|---|
| 3,100,778 | * 8/1963 | Berman | 260/319 |
| 3,501,410 | * 3/1970 | Newland et al. | 252/300 |
| 4,220,708 | 9/1980 | Heller | 430/336 |
| 4,225,661 | * 9/1980 | Muzyczko | 430/156 |
| 4,882,438 | 11/1989 | Tanaka et al. | 548/407 |
| 5,532,361 | 7/1996 | Allegrini et al. | 544/70 |
| 5,543,533 | * 8/1996 | Allegrini et al. | 549/389 |

OTHER PUBLICATIONS

Chemical Abstract vol. 110 No. 85.587, Omote et al. "Spiropyran Photochromic Material and Its Coloration", 1988.*
Abrahart, "Dyes and Their Intermediates", 1968, Pergamon Press p. 8.*

Intelligent Gels—Using solvent–swollen polymer networks that respond to stimuli, scientists are beginning to develop a soft, wet, organic technology; By: Ron Dagani; Dated: Jun. 9, 1997 C&EN; pp. 26–37.

Fujimura et al, Chemical Abstract vol. 112 No. 129229, "Thermochromic Recording Materials" Mar. 7, 1988.*

Arai et al, Chemical Abstract vol. 124 No. 215776, "Prep. of Photochromic Spiropyrans Linked to Methyl Cellulose & Photoregulation" 1996.*

* cited by examiner

Primary Examiner—John Kight
Assistant Examiner—Raymond Covington
(74) Attorney, Agent, or Firm—Faegre & Benson LLP

(57) ABSTRACT

The present invention provides water-soluble, pyran-based photochromic compounds characterized by improved stability when in an open, excited configuration. The advantages of the present invention are provided, at least in part, by functionalizing a pyran-based photochromic compound with carboxylate functionality in such a way that the carboxylate and/or its counter ion have sufficient mobility to engage in intermolecular and intramolecular interactions. In preferred embodiments, such a mobile carboxylate and/or counter ion provided on one side of an open pyran ring is preferably capable of complexing with functionality on the other side of the open pyran ring, greatly stabilizing the open configuration.

51 Claims, 9 Drawing Sheets

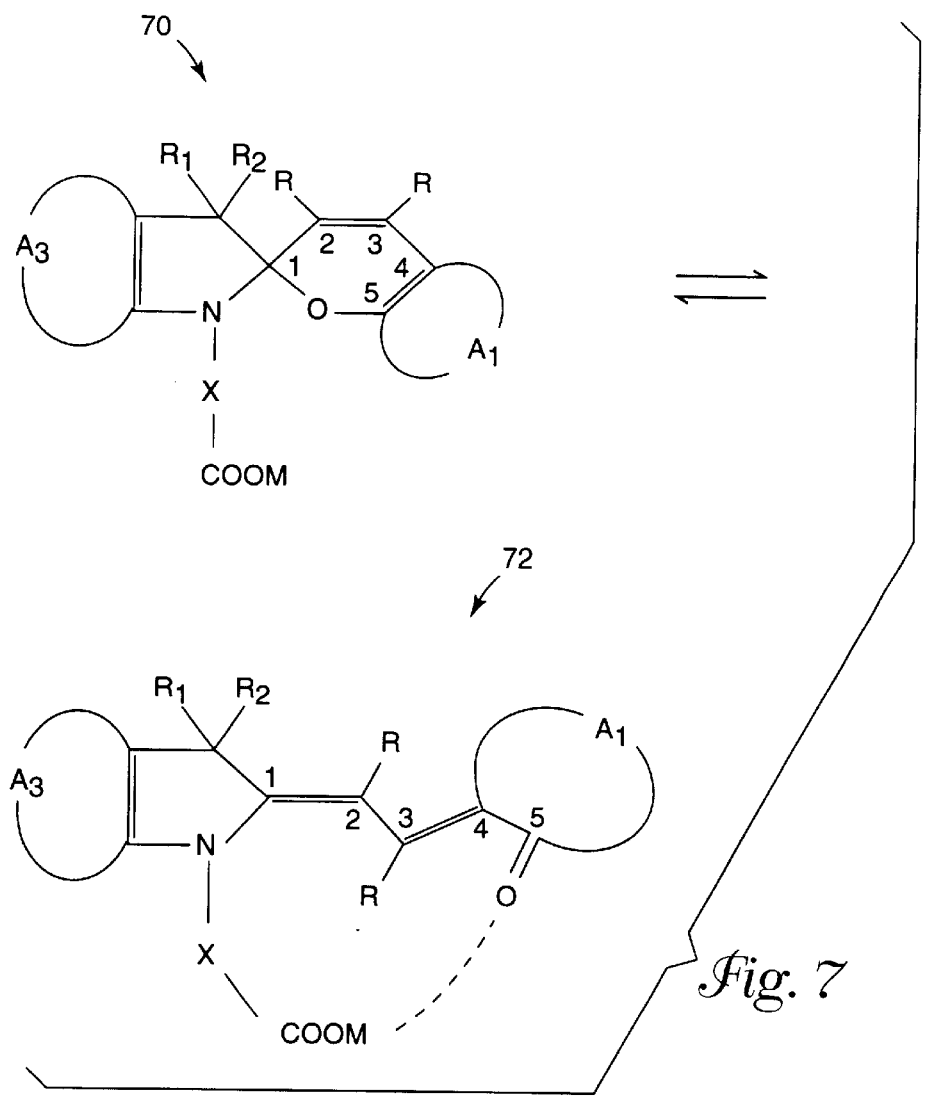
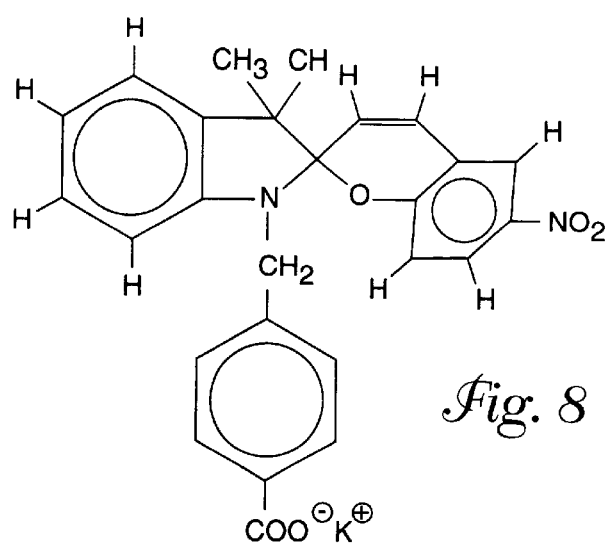
Fig. 7
Fig. 8

WATER SOLUBLE, PYRAN-BASED PHOTOCHROMIC COMPOUNDS HAVING CARBOXYLATE FUNCTIONALITY

The present application claims the benefit of priority from U.S. Provisional application Ser. No. 60/044,149, filed Apr. 23, 1997, incorporated herein by reference.

FIELD OF THE INVENTION

The present invention relates to compounds displaying photochromic behavior and more particularly to water soluble photochromic compounds of the type comprising a pyran ring which is closed in a ground state and open in an excited state. The present invention also relates to methods for preparing these compounds.

BACKGROUND OF THE INVENTION

Photochromic compounds are compounds which can reversibly change color and/or degree of light transmission when they are exposed to a source of exciting electromagnetic radiation, e.g., visible light or ultraviolet light most commonly. The compounds return to their original state of color and/or light transmission when the exposure source is removed and/or the compound is exposed to counteracting light. Many forms of photochromic compounds are known. For example, U.S. Pat. Nos. 3,100,778; 3,501,410; 4,220,708; 4,882,438; 5,532,361; and 5,543,533 describe a variety of photochromic structures.

One class of photochromic compounds are pyran-based in that these compounds incorporate a pyran moiety. Color changes in such compounds result from configurational changes in the pyran moiety. In one form corresponding to the ground state, the pyran moiety is closed and forms a six membered ring. Pyran-based photochromic compounds in the ground state are most commonly colorless. In another form corresponding to the excited state, exposure to light causes the pyran ring to open up. Pyran-based photochromic compounds in the excited, open state exhibit a second state of color. For example, some of the previously known pyran-based photochromic compounds display yellow, yellow-orange, or blue colors when in the excited configuration.

The closed configuration is generally more stable than the open configuration. Accordingly, in the absence of an exciting source of radiation, pyran-based compounds in the open state tend to revert back to the closed configuration. To help stabilize the open configuration, the pyran moiety is typically linked to moieties having extended π-electronic systems. These stabilizing moieties are linked to the pyran ring in such a way that at least one such stabilizing moiety is linked to one side of the open pyran ring, and at least one other is linked to the other side of the open pyran ring. Examples of such compounds are known and have been described in U.S. Pat. Nos. 3,100,778; 3,501,410; 5,532,361; and 5,543,533.

Stability of pyran-based photochromic compounds still remains a concern, however. Many of the pyran-based compounds fade from a colored state to a colorless state too quickly. In other materials, a lack of stability is evidenced by weak colors. There is a need, therefore, for pyran-based photochromic compounds having greater stability and that display more vibrant, pure colors.

Temperature dependence is another concern. Many pyran-based photochromic compounds display photochromic properties only at temperatures well above or below ambient conditions. It would be desirable if such compounds could display photochromism over a wide temperature range, including ambient temperatures.

Many of the previously known photochromic compounds also lack water solubility, preventing their use in aqueous systems. Still others are made by reaction schemes having low yields, affecting the efficiency and economics of manufacture.

SUMMARY OF THE INVENTION

The present invention provides pyran-based photochromic compounds characterized by improved stability when in an open, excited configuration. As a consequence, photochromic compounds of the present invention display extremely vibrant, stable colors which can be red, pink, purple, orange, or the like depending upon how the principles of the invention are implemented. The photochromic compounds of the invention also are substantially water soluble, making them suitable for use in aqueous systems if desired. Additionally, photochromic compounds of this invention exhibit photochromism over a wide temperature range, including ambient temperatures. As still yet another advantage, the photochromic compounds of this invention can be made according to reaction schemes characterized by very high yields.

The advantages of the present invention are provided, at least in part, by functionalizing a pyran-based photochromic compound with carboxylate functionality in such a way that the carboxylate has sufficient mobility to engage in intermolecular and intramolecular interactions. In preferred embodiments, such a mobile carboxylate provided on one side of an open pyran ring is preferably capable of complexing with functionality on the other side of the open pyran ring, greatly stabilizing the open configuration.

In one aspect, the advantages of the present invention are achieved by an ionic photochromic compound, comprising:

(a) a pyran moiety comprising oxygen as a ring constituent;

(b) an aromatic moiety comprising an aromatic ring fused to the pyran moiety;

(c) at least one heterocyclic ring moiety linked to the pyran moiety at an ortho position relative to the oxygen ring constituent; and (d) at least one carboxylate moiety linked to the heterocyclic ring moiety.

In another aspect, the present invention provides a method of making an ionic photochromic compound, comprising the steps of:

(a) providing a reactant comprising a heterocyclic ring including a nitrogen atom as a ring constituent and comprising an aromatic moiety having an aromatic ring fused to the heterocyclic ring;

(b) attaching a carboxyl moiety to the nitrogen atom in a manner such that the carboxyl moiety is linked to the nitrogen atom by a divalent linking group;

(c) providing an aromatic reactant comprising an aromatic ring having substituents reactive with the product of step (b) to form a reaction product comprising a pyran ring having an oxygen atom as a ring substituent and a saturated carbon atom ortho to the oxygen atom, said substituents being reactive such that the aromatic ring of the aromatic ring is fused to the resultant pyran ring and the saturated carbon atom of the pyran ring ortho to the oxygen atom is linked to the heterocyclic ring; and (d) reacting the product of step (b) with the aromatic reactant under conditions effective to form said pyran ring, whereby the ionic photochromic compound is formed.

BRIEF DESCRIPTION OF THE DRAWINGS

The above mentioned and other advantages of the present invention, and the manner of attaining them, will become more apparent, and the invention itself will be better understood, by reference to the following description of the embodiments of the invention taken in conjunction with the accompanying drawings, wherein:

FIG. 7 is a more detailed illustration of the photochromic compounds of FIG. 5;

FIG. 8 is an example of a specific photochromic compound of the present invention of the type shown in FIGS. 5–6;

DETAILED DESCRIPTION OF THE PRESENTLY PREFERRED EMBODIMENTS

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

Figure 1:
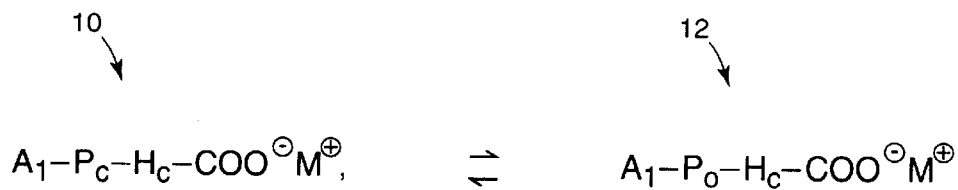
FIG. 1 shows the general structure of photochromic compounds of the present invention in both the ground and excited configurations.

FIG. 1 shows a general structure of one embodiment of a photochromic compound of the present invention. The embodiment is depicted in a ground configuration 10 and an excited configuration 12. The compound may be converted from ground configuration 10 to excited configuration 12 upon exposure to a suitable source of exciting radiation, such as ultraviolet light. The compound may be reversibly converted from the excited configuration 12 back to the ground configuration 10 by removing the source of light in some embodiments, or by exposing the excited compound to a different kind of light in other embodiments.

Photochromic compounds of the present invention visually display a different color in each of configurations 10 and 12. Most typically, the compounds are colorless in the ground configuration 10 and brightly colored in the excited configuration 12. The hue and strength of color shown in either configuration will depend upon a variety of factors, including the particular structure of the compound being used, the type of solvent in which the compound is dispersed, the type of light being used for exposure, and the like.

Referring now to the ground configuration 10 shown in FIG. 1, photochromic compounds in the ground state incorporate a closed, pyran ring moiety $P_c$. According to the present invention, a pyran ring moiety is a substantially planar, six-member ring comprising oxygen and five carbon atoms as ring constituents. A closed pyran ring may have as many as five ring substituents linked to each of the carbon atoms, although a lesser number may be present if one or more ring substituents are fused to the pyran ring moiety. Aromatic moiety $A_1$ comprises an aromatic ring which is fused to the ring, preferably at the carbon atoms of the pyran moiety which are at ortho and meta positions in one direction from the oxygen ring constituent. The compound further comprises heterocyclic moiety $H_c$ which includes a heterocyclic ring linked to the pyran ring moiety at the pyran carbon ring constituent which is at the ortho position in the other direction from the pyran oxygen atom. Carboxylate moiety —COO$^\ominus$M$^\oplus$ is linked to the heterocyclic moiety $H_c$ either directly by a single bond or indirectly through a divalent linking group. M$^\oplus$ may be any monovalent, positively charged counter cation effective for providing electrical neutrality. Representative examples of moieties suitable for use as M$^\oplus$ include H$^\oplus$, Na$^\oplus$, Li$^\oplus$, K$^\oplus$, NH$_4^\oplus$, H—NR$_3^\oplus$, combinations of these, and the like, wherein each R is a monovalent substituent, preferably comprising 1 to 30 carbon atoms, more preferably a lower alkyl group of 1 to 4 carbon atoms such as ethyl.

Excited configuration 12 corresponds to ground configuration 12, except that the pyran ring is in an open configuration, designated as $P_o$. Aromatic moiety $A_1$ and heterocyclic moiety $H_c$ provide extended $\pi$-electronic systems which help stabilize the open pyran ring $P_o$. In the excited configuration 12, photochromic compounds of the present invention exhibit exceptionally vibrant colors.

In accordance with the present invention, the carboxylate moiety —COO$^\ominus$M$^\oplus$ is linked to the pyran ring $P_o$ or $P_c$, as the case may be, through a flexible linkage which provides the carboxylate moiety with a relatively high degree of mobility to move around and engage in intermolecular and/or intramolecular interactions. Such flexible linkage can either be a flexible moiety coupling the carboxylate moiety to the heterocyclic ring in the event that the heterocyclic ring is attached to the pyran ring by a relatively immobile bond such as a fused spiro linkage. Alternatively, the flexible linkage can include the heterocyclic ring in the event that the heterocyclic ring is attached to the pyran ring by a flexible bond such as a single bond.

The flexible linkage between the carboxylate moiety and the rest of the photochromic compound provides numerous advantages. Firstly, the polar character of the carboxylate helps to make the photochromic compounds of the present invention very water soluble, which is a trait not shared by many other kinds of photochromic compounds. The group also provides photochromic compounds with extremely vibrant, stable color properties when exposed to an exciting source of light.

While not wishing to be bound, a possible theory to explain the improved color performance of the present invention can be suggested. It is believed that the flexible linkage with the carboxylate moiety allows the counter ion of the carboxylate to complex with the quinone-type oxygen atom of the open pyran ring. Such complexing, if it occurs, would greatly stabilize the open, excited configuration 12, thus producing the stable, vibrant colors observed with photochromic compounds of this invention. In contrast, if a photochromic compound lacks a carboxylate group, or includes one on a relatively inflexible linkage, the resultant colors displayed are less intense than and do not last as long as those of the present invention, strongly supporting the hypothesis that compounds lacking the flexible linkage are much less stable in the open configuration than the compounds of the present invention.

Figure 2:
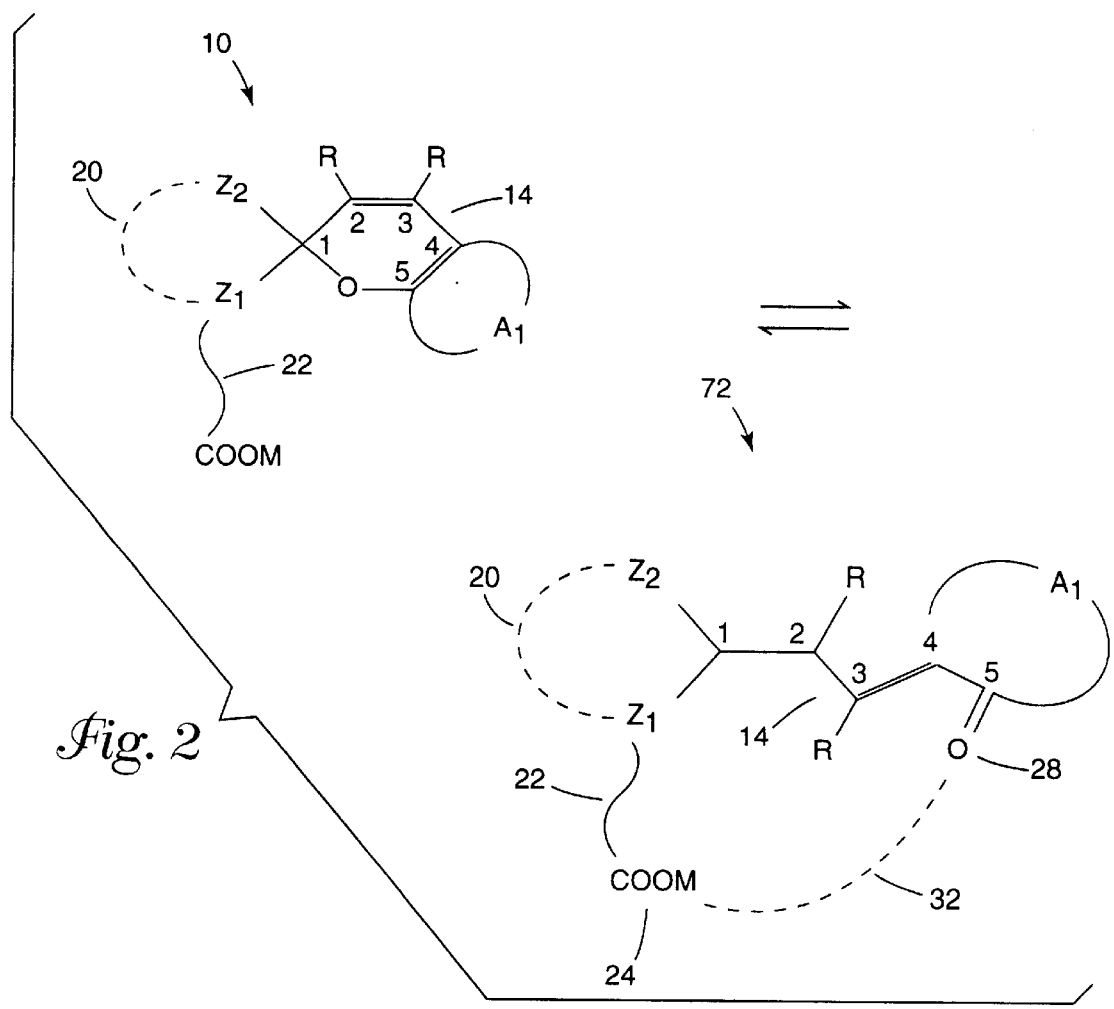
FIG. 2 is a more detailed illustration of the photochromic compounds of FIG. 1.

FIG. 2 shows the corresponding ground configuration 10 and open configuration 12 of the preferred class of photochromic compounds in more detail. Referring first to ground configuration 10, pyran ring 14 is closed. Pyran ring 14 includes an oxygen atom and five carbon atoms. The position of each carbon atom has been designated by numbers 1 through 5 and shall be referred to herein as the C1 through C5 positions, respectively. The carbon atoms at the C4 and C5 positions are fused to an aromatic ring of aromatic moiety $A_1$. Aromatic moiety $A_1$ may be any aromatic moiety capable of contributing an extended π-electronic structure to help stabilize the pyran ring 14 when in its open configuration. For example, $A_1$ can be a substituted or unsubstituted phenyl moiety, a substituted or unsubstituted naphthyl moiety, an aromatic heterocyclic moiety, other multi-ring moieties including a plurality of aromatic rings linked to each other by fused and nonfused bonds, and the like.

Figure 3A:
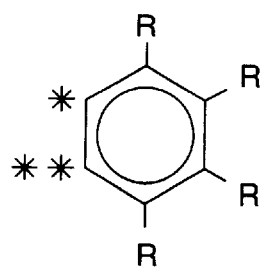
FIGS. 3a through 3d show examples of aromatic moieties suitable for use as the aromatic moiety $A_1$ of FIG. 1.
Figure 3B:
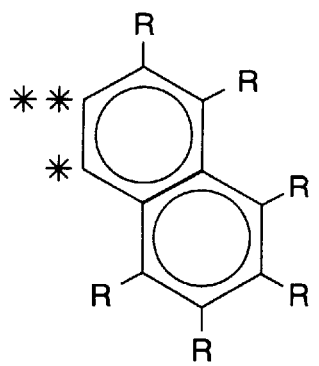
Figure 3C:
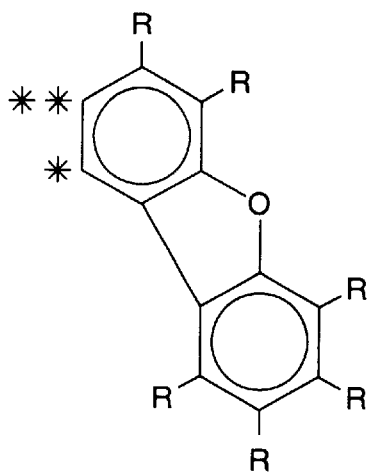
Figure 3D:
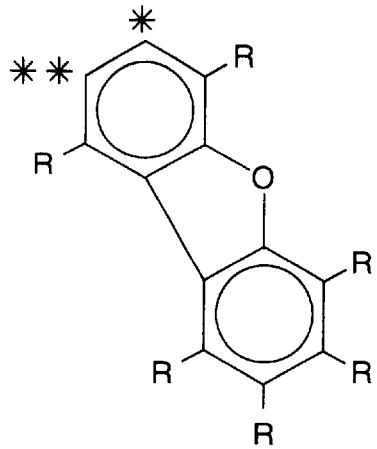

Representative examples of aromatic moieties suitable for use as $A_1$ are shown in FIGS. 3a, 3b, 3c, and 3d. In each of these Figures, the carbon atoms denoted with the "**" symbols are also the pyran carbon at the 5C position, and the carbon atoms denoted with the "*" symbol are also the pyran carbon at the 4C position. In each of the embodiments of $A_1$ shown in the Figures, each R may be independently selected from any suitable monovalent substitiuents or cyclic substituents in which pairs of R moieties are co-members of a ring structure. Representative examples of moieties suitable for use as each R include hydrogen, halogen, alkyl, aryl, aralkyl, aryloxy, alkoxy, hydroxy alky, amino, ammonium, piperidino, morpholino, carboxy, carboxyamido, cyana, nitro, hydroxyl, alkenyl, cycloalkyl, piperazino, carboxyalkyl, a sulphonic group, a sulfate group, a phosphonate group, a phosphate group, an acyl group, and combinations thereof Any of such moieties, if cyclic, can include a plurality of rings if desired. For example, aryl moieties could be aryl-aryl structures. In the case of the embodiment of FIG. 3a one R is preferably a substituent such as —$NO_2$ and the other R groups are each preferably hydrogen. More preferably, the substituent such as —$NO_2$ is at the para position relative to the carbon atom denoted with the "**" symbol. In FIGS. 3b, 3c, and 3d, each R is preferably hydrogen or an alkoxy group such as —$OCH_3$.

Referring again to FIG. 2, each of the R substituents attached to the C2 and C3 carbons of the pyran ring 14 is independently any suitable monovalent moiety such as the kinds of moieties suitable for use as R defined in connection with FIGS. 3a through 3d. Most preferably, however each of the R substituents attached to the C2 and C3 carbons of the pyran ring is hydrogen.

The $Z_1$ and $Z_2$ moieties are linked to the C1 carbon of the pyran ring 14. In some embodiments of the present invention, $Z_1$ and $Z_2$ may be separate moieties linked to the C1 carbon by a single bond, respectively. In such embodiments, $Z_1$ is a heterocyclic moiety comprising a heterocyclic ring, and $Z_2$ is a moiety having an extended π-electronic structure and may be selected from an aromatic moiety, an aromatic heterocyclic moiety, or a heterocyclic moiety comprising a heterocyclic ring. One representative example of a heterocyclic moiety suitable for use as $Z_1$ and optionally $Z_2$ in such embodiments is the thiophenyl ring moiety shown in FIG. 4a. There, the single bond denoted with the "*" symbol is linked to the C1 carbon of the pyran moiety; the single bond denoted by the "**" symbol is linked to the carboxylate moiety; and $R_3$ and $R_4$ are each independently a monovalent moiety or, in combination, co-members of a ring structure fused to the thiophenyl ring. When $Z_2$ is not heterocyclic moiety, then one example of an aromatic moiety suitable for use as $Z_2$ is a substituted or unsubstituted phenyl group.

In other embodiments of the invention, $Z_1$ and $Z_2$ may be comembers of a heterocyclic ring moiety. Such structure is shown schematically in FIG. 2 by the dotted line 20. In such embodiments, the C1 carbon of the pyran ring 14 is shared by both the pyran ring and the $Z_1/Z_2$ ring. Such a linkage between rings is referred to in the art as a "spiro linkage". One representative example of a heterocyclic moiety suitable for use as a $Z_1/Z_2$ ring is the pyrrolidine type ring moiety shown in FIG. 4b. There, the carbon atom denoted by the symbol "*" is also the C1 carbon atom of the pyran ring 14; the carbon atoms denoted by the symbol "" are fused to an aromatic ring of an aromatic moiety; the single bond denoted by the "*" symbol is linked to the carboxylate moiety directly or by a divalent linking group; and each of $R_1$ and $R_2$ is independently a monovalent moiety other than H or an acidic group or are co-members of a cyclic ring structure. Preferably, each of $R_1$ and $R_2$ is a lower alkyl group of 1 to 4 carbon atoms, such as —$CH_3$.

Figure 4A:
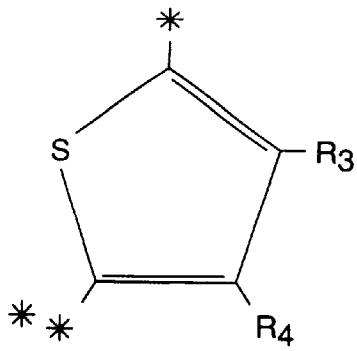
FIGS. 4a and 4b show examples of heterocyclic moieties suitable for use as the heterocyclic moiety $H_c$ in FIG. 1.
Figure 4B:
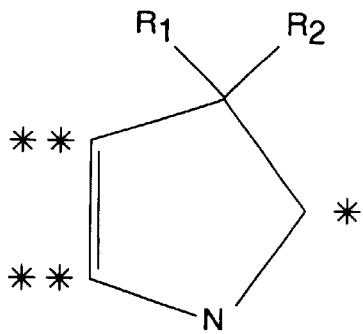

In addition to the heterocyclic ring moieties shown in FIGS. 4a and 4b, a wide variety of other heterocyclic structures could also be advantageously used in the present invention. Representative examples include moieties based on picoline, collidine, benzofuran, benzothiophene, carbazole, tryptophan, bromoquinoline, nitroquinoline, quinoline, nicotine, quinaldine, triphenylpyrazole, nitroisoquinoline, pyridine, oxazole, imadazole, thiazole, isoxazole, pyrazole, furan, pyrrole, thiophene, and the like.

Carboxylate moiety 24 is linked to $Z_1$ by linkage 22. Linkage 22 may be a single bond or a divalent linking group. Generally, if $Z_1$ and $Z_2$ are co-members of a ring structure as is the case with the $Z_1/Z_2$ ring embodiment shown in FIG. 4b, then linkage 22 is desirably a divalent linking group to ensure that carboxylate moiety 24 will have sufficient flexibility. On the other hand, if $Z_1$ and $Z_2$ are separate moieties, then linkage 22 can be a single bond because $Z_1$ would then tend to provide a linkage between carboxylate moiety 24 and pyran ring 14 with sufficient flexibility to achieve the objectives of this invention.

Still referring to FIG. 2, the excited configuration 12 of the compound is substantially similar to the ground configuration 10, except that pyran ring 14 has opened in response to exposure to incident light. As shown, the oxygen atom of open pyran ring 14 forms quinone-type oxygen 28. Further, the quinone-type oxygen 28 is schematically shown as being complexed to the carboxylate moiety 24 by dotted line 32.

Figure 5:
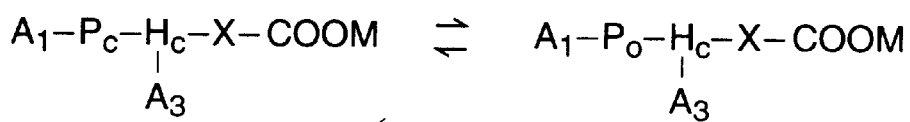
FIG. 5 shows the general structure of a preferred photochromic compound of the present invention.

FIG. 5 shows the general structure of a particularly preferred embodiment of a photochromic compound of the present invention. The embodiment is depicted in a ground configuration 50 and an excited configuration 52. The embodiment of FIG. 5 is similar to the embodiment of FIG. 1, except that the embodiment of FIG. 5 specifically includes the moiety $A_3$ which is attached to the heterocyclic moiety $H_c$ and further includes divalent linking group X. Further, $H_c$ is linked to $P_c$ by a spiro linkage. Otherwise, each of $A_1$, $P_c$, $P_o$, $H_c$, X, and —$COO^\ominus M^\oplus$ are as defined above.

$A_3$ may be any aromatic moiety having an aromatic ring which is preferably fused to the heterocyclic moiety. As one representative example, $A_3$ may be a substituted or unsubstituted benzene ring. Thus, the valent sites of the benzene ring not fused to the heterocyclic moiety may be provided with any monovalent or cyclic ring substituent, as desired. Generally, any of the moieties suitable for use as the R moieties defined above could also be used as substituents on the benzene ring as well. Preferably, each of such substituents is hydrogen.

The divalent linking group X can be any divalent moiety capable of linking the carboxylate group to the heterocyclic moiety $H_c$. Preferably, X is a moiety comprising 4 to 20, and more preferably 4–10 carbon atoms. One example of a divalent moiety particularly suitable for use as X is the divalent moiety shown in FIG. 6. There, the valent sites of the moiety which are not used for linking may be provided with R substituents as defined above. In particularly preferred embodiments, each such valent site is provided with hydrogen as a substituent.

Photochromic compounds according to FIG. 5 display very beneficial, vibrant colors. The color properties of these compounds are highly dependent upon the environment in which such compounds are used. For example, in water, there is a significant concentration of the open, colored form, so the solution is bright red. The solution turns colorless when exposed to sunlight and turns back to red when removed from the sunlight. This is extraordinarily unusual in that these compounds thus exhibit reverse photochromism in water.

In dilute DMSO solutions, the compounds are colorless until exposed to ultraviolet light. When removed from the ultraviolet light, or put in sunlight, the compounds are again colorless. In concentrated DMSO solutions, the compounds are a deep purple/red. In sunlight, the compounds become colorless. Thus, concentrated solutions of these compounds in DMSO exhibit reverse photochromism.

When the components are dispersed in a nonpolar polymer matrix (e.g., a styrene based polymer) to form coatings, the coatings are colorless. But, when exposed to ultraviolet light or sunlight, the coatings turn pink. Take away such light, the coatings turn purple and then gradually fade to colorless. When the compounds are dispersed in a polar polymer matrix (e.g., a polyurethane) to form coatings, the coatings are colorless until exposed to ultraviolet light. Exposure to sunlight then turns the coatings back to a colorless state.

FIG. 7 shows a preferred structure for the compounds of FIG. 5. The preferred structure is shown in a ground configuration 70 in which the pyran ring is closed and an excited configuration 72 in which the pyran ring is open. In the configurations 70 and 72, $A_1$, $A_3$, R, $R_1$, $R_2$, X and $M^{\oplus}$ are as defined above. A particularly preferred embodiment of a compound in accordance with FIG. 7 is shown in FIG. 8.

Figure 9:
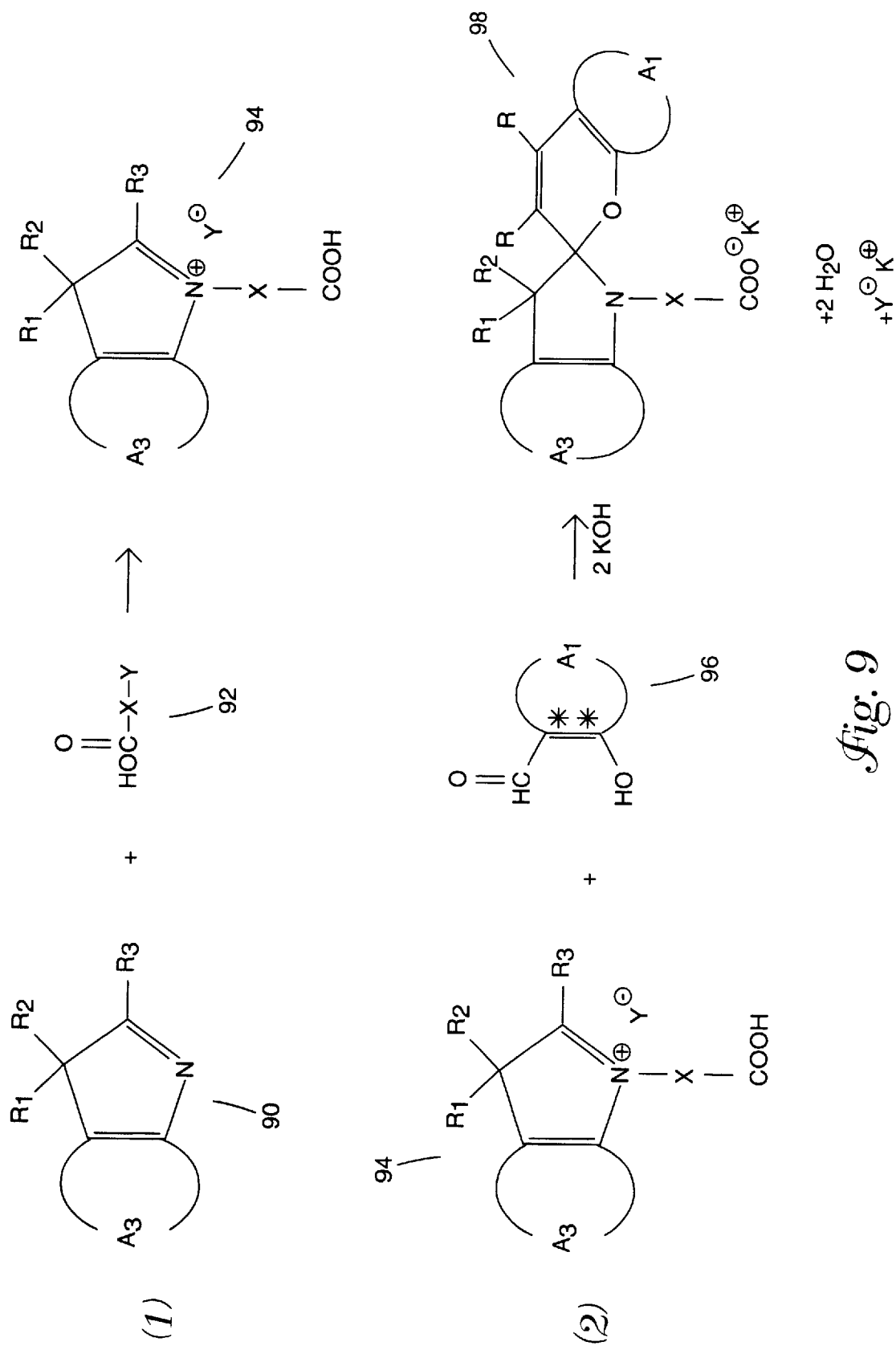
FIG. 9 shows a reaction scheme for making the compounds of FIGS. 5–8.

One approach for making compounds according to FIGS. 5, 7, and 8 is shown in FIG. 9. A two step reaction scheme is shown. In the first reaction step, reactant 90 is a compound comprising an aromatic heterocyclic ring including a nitrogen atom as a ring constituent. Aromatic moiety $A_3$, as defined above, includes an aromatic ring fused to the heterocyclic ring. $R_1$ and $R_2$ may be monovalent substituents or co-members of a ring structure as defined above, but each is preferably —$CH_3$. $R_3$ may be

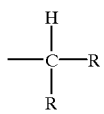

wherein each R' is independently a monovalent substituent, wherein R has been defined herein. Preferably, $R_3$ is an alkyl group of 1 to 4 carbon atoms or -$a_1$,-$a_2$, wherein $a_1$ is an alkylene moiety and $a_2$ is an aromatic moiety. Most preferably, $R_3$ is —$CH_3$. A specific example of a preferred compound having a structure in accordance with reactant 90 is 2,3,3-trimethylindoline.

In the first reaction step, a carboxylate moiety is attached to the nitrogen atom through a divalent linking group X, as defined above. According to a preferred method to accomplish this, reactant 90 is reacted with carboxylate functional compound 92. In compound 92, X is the divalent linking group, and Y is selected from a halogen atom and a tosylate.

Figure 6:
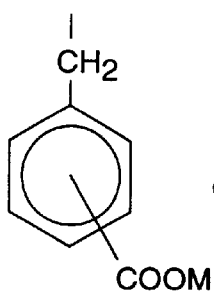
FIG. 6 shows one example of a divalent moiety suitable for use as divalent moiety X in FIG. 5.

Preferably, X is a divalent moiety according to FIG. 6, and Y is bromine. A specific compound having a structure in accordance with reactant 92 is α-bromotoluic acid.

According to one set of reaction conditions found to be suitable for carrying out the first reaction step, approximately equimolar quantities of reactants 90 and 92 are combined in a suitable solvent such as acetonitrile ($CH_3CN$) and then refluxed under an inert atmosphere such as $N_2$, argon, or the like, until the reaction is complete. The reaction product is obtained as an off-white precipitate having a structure in accordance with intermediate reaction product 94. The product is recovered by filtration and washed with chloroform.

In the second reaction step, the intermediate reaction product 94 of the first reaction step is reacted with an aromatic compound 96 having an aromatic ring with ring substituents reactive with compound 94 to form a photochromic compound incorporating a pyran ring as described above. As shown in the Figure, a preferred aromatic compound is reactant 96. With regard to reactant 96, $A_1$ is an aromatic moiety as defined above, and the carbon atoms denoted with the "*" symbols are substituents of an aromatic ring. A specific example of one such compound found to be suitable in the practice of the present invention is 2-hydroxy-5-nitrobenzaldehyde.

According to one set of conditions found to be suitable for reacting compounds 94 and 96 together, a base such as KOH, NaOH, or the like, is added to a suitable solvent such as ethanol. Generally, at least two equivalents of base are used for each equivalent of compound 94. Compound 94 is added to the solution, and then reactant 96 is added. Generally, equimolar amounts of compound 94 and reactant 96 are used. The mixture is then refluxed under an inert atmosphere until the reaction is completed. The resultant reaction product is the photochromic compound 98. Additional reaction products include water and counterions as shown. To recover photochromic compound 98, the reaction mixture is cooled to about room temperature. Crystals of compound 98 form and may be recovered by a suitable technique such as vacuum filtration.

Figure 10:
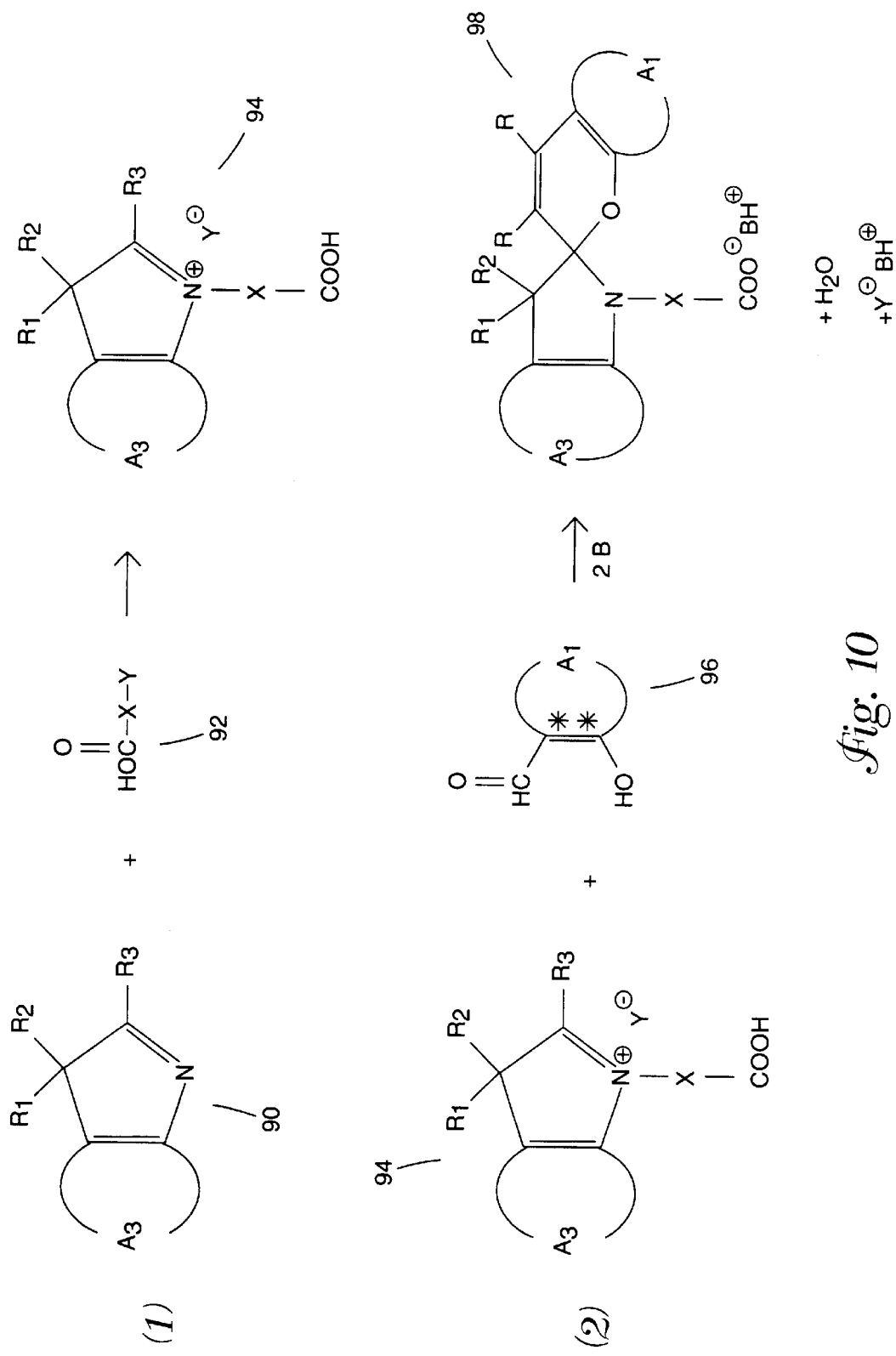
FIG. 10 shows an alternative reaction scheme for making the compounds of FIGS. 5–8.

An alternative reaction scheme for making a compound having the same general structure as photochromic compound 98 is shown in FIG. 10. The reaction scheme of FIG. 10 is identical to the reaction scheme of FIG. 9 except that a neutral base, such as triethylamine, is used in the second reaction step. As an additional difference, less water is produced, and the resultant ions are different than those resulting in FIG. 9. Advantageously, the reaction scheme of FIG. 10 is characterized by substantially 100% yield with no byproduct.

Figure 11:
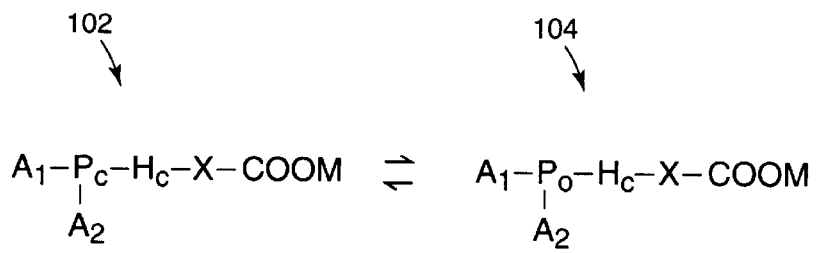
FIG. 11 shows the general structure of another preferred photochromic compound of the present invention.

FIG. 11 shows the general structure of another particularly preferred embodiment of the present invention. The embodiment is depicted in its ground configuration 102 and its excited configuration 104. The embodiment of FIG. 11 is similar to the embodiment of FIG. 5, except that the embodiment of FIG. 5 does not include the $A_3$ moiety. Instead, FIG. 11 includes an $A_2$ moiety which is linked to the C1 carbon of pyran ring $P_c$ or $P_o$, as the case may be, by a single bond. In the practice of the present invention, $A_2$ may be any moiety including and an extended π-electronic structure. Representative examples of moieties suitable for use as $A_2$ include an aromatic moiety, a heterocyclic moiety, an aromatic heterocyclic moiety, or the like. In preferred embodiments, $A_2$ is a substituted or unsubstituted benzene ring linked to the C1 carbon of the pyran ring by a single bond. Generally, any of the R substituents defined above could be used as substituents on $A_2$ as well. Preferably, however, all of such substituents on $A_2$ are hydrogen. Each of $A_1$, $P_o$, $P_c$, $H_c$, X, and $COO^{\ominus}M^{\oplus}$ may be moieties as defined above.

Figure 12:
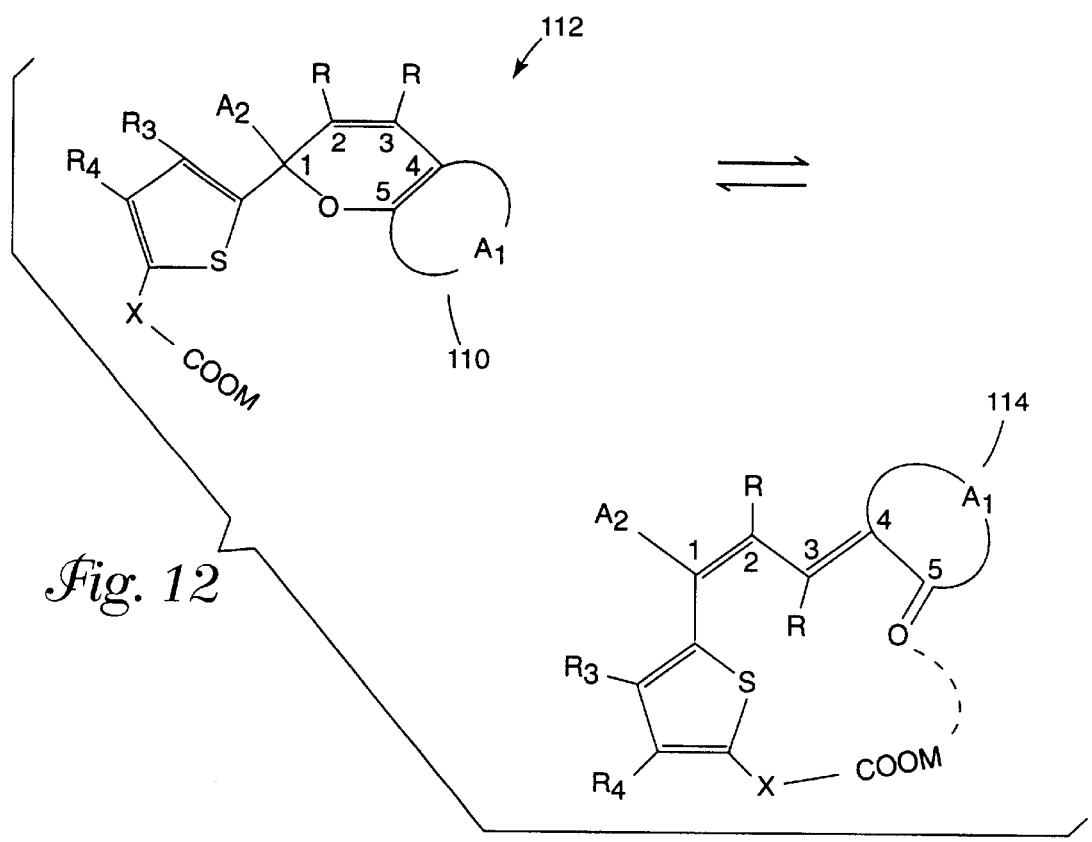
FIG. 12 is a more detailed illustration of the photochromic compound of FIG. 11.

FIG. 12 shows a preferred structure for the compounds of FIG. 11. The preferred structure has a ground configuration 110 in which pyran ring 112 is closed and excited configuration 114 in which pyran ring 112 is opened. In FIG. 12, $A_1$, $A_2$, R, $R_3$, $R_4$, X, and $COO^\ominus M^\oplus$ are as defined above.

Figure 13:
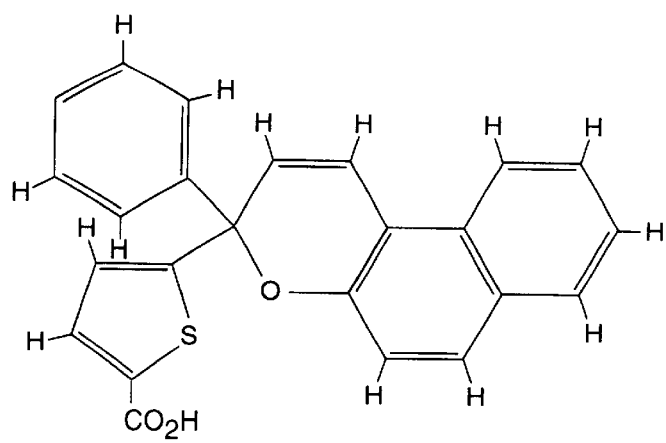
FIG. 13 is an example of a specific photochromic compound of the present invention of the type shown in FIGS. 11–12.
Figure 14:
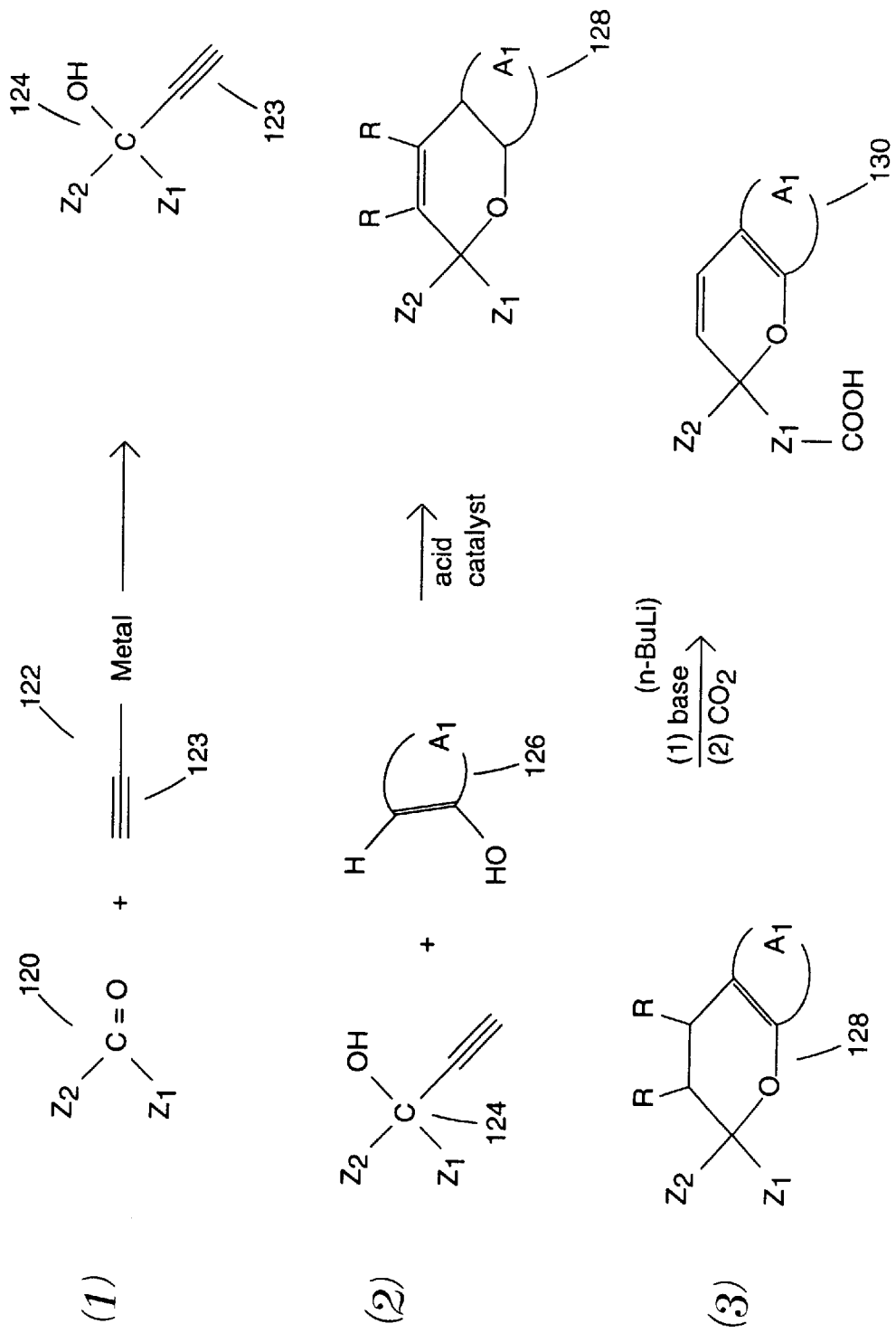
FIG. 14 shows a reaction scheme for making the compounds of FIGS. 12–13.

One approach for making compounds according to FIGS. 11, 12, and 13 is shown in FIG. 14. FIG. 14 shows a three-step reaction scheme. In the first reaction step, a first reactant 120 includes moieties $Z_1$ and $Z_2$ (defined above) linked to each other via a carbonyl group. A second reactant 122 is an organometallic compound comprising a carbon-carbon triple bond 123. The first and second reactants 120 and 122 are reacted together to form intermediate reaction product 124 having pendant hydroxyl and pendant triple bond functionality. Suitable reaction conditions for carrying out this reaction step includes reacting the first and second reactants 120 and 122 together in a suitable solvent, such as THF, at room temperature.

In a second reaction step, intermediate reaction product 124 is reacting with an aromatic compound 126 having OH functionality pendant from an aromatic ring. In the figure, aromatic compound 126 is generally designated $A_1$, wherein $A_1$ may be the aromatic moiety $A_1$ as defined above. The intermediate reaction product 124 and the aromatic compound 126 react to form photochromic compound 128 of the type shown in FIGS. 11 and 12, except that photochromic compound 128 lacks carboxylate functionality in accordance with the present invention. Suitable reaction conditions for carrying out this reaction step include reacting the intermediate reaction product 124 and the aromatic compound 126 together in a suitable solvent such as benzene using p-toluenesulfonate ("PTSA") as a catalyst at reflux.

The third reaction step involves attaching carboxylate functionality to $Z_1$. Because the heteroatom of the heterocyclic moiety $Z_1$ causes an adjacent valent site to be so much more reactive than other valent sites on compound 126, particularly if the substituent on the adjacent valent site is hydrogen, the carboxylate can be attached to $Z_1$ with very high efficiency. According to one approach for carrying out this third reaction step, photochromic compound 26 is reacted with a base such as n-butyl lithium and then quenched with $CO_2$. As alternatives to n-butyl lithium, other bases such as t-butyl lithium, lithium diisopropylamide, potassium hydride, lithium hydride, or the like, may be used. As alternatives to $CO_2$, an anhydride, a halo carboxylate, or the like, may be used. The reaction product is a carboxyl functional photochromic compound 130 in accordance with the present invention. Suitable reaction conditions for carrying out this reaction step include using THF as solvent and carrying out the reaction at -78° C.

Figure 15:
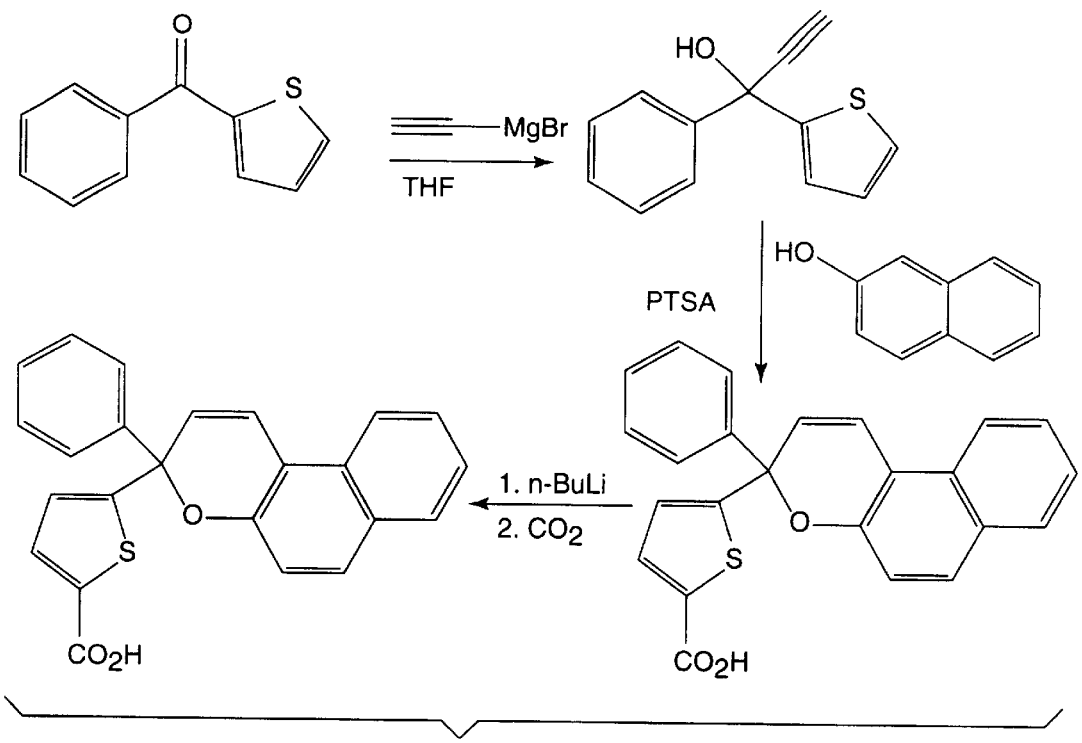
FIG. 15 is shows the use of specific compounds in the reaction scheme of FIG. 14.

FIG. 15 shows a particularly preferred application of the reaction scheme of FIG. 14 to specific compounds.

Photochromic compounds of the present invention according to FIGS. 11–15 also display colors upon exposure to particular kinds of exciting light. For example, dissolving the photochrome of FIG. 15 in basic water produced a slightly yellow solution which, when irradiated with ultraviolet light, turned pink.

The present invention will now be further described with reference to the following examples.

EXAMPLE 1

To a flame dried 500 mL flask containing a stir bar was added α-bromotoluic acid (3.25 g, 0.015 mole) and 200 mL of $CH_3CN$. This mixture stirred until the solid dissolved. To this stirring solution was added 2,3,3 trimethylindoline (2.4 g, 0.015 mole). The solution was then refluxed under a $N_2$ atmosphere for 15 hours. After cooling to room temperature the precipitate was filtered off and washed with chloroform to yield the product (5.6 grams, 0.015 mol, 100%) as an off-white solid.

EXAMPLE 2

To a flame dried 50 mL flask containing a stir bar was added KOH (0.37 g, $6.67 \times 10^{-3}$ mol) and 10 mL of absolute ethanol. This mixture stirred until the KOH dissolved. Compound 1 (1 g, $2.67 \times 10^{-3}$ mol) was added and then 2-hydroxy-5-nitrobenzaldehyde (0.45 g, $2.67 \times 10^{-3}$ mol) was added. The mixture refluxed overnight under a blanket of $N_2$. After cooling to room temperature crystals formed and were removed by vacuum filtration. These crystals were the product.

EXAMPLE 3

In each of the reactions performed below, anhydrous conditions were used, unless otherwise specified. All glassware was flame-dried and cooled under positive nitrogen pressure. All reactions were also kept under positive nitrogen pressure. All reactants were purchased from Aldrich Chemical Company; non-anhydrous ether used in extraction was purchased from Fischer Chemical Company. A Bruker 300 MHz Nuclear Magnetic Resonance Spectrophotometer was used in the determination of products. Synthesis of 2,2'-difuryl methanol. 45.42 mL (0.6244 mol) of furan were placed via syringe into a round bottom flask containing a stir bar, and 20 mL of anhydrous ether and 20 mL of anhydrous Tetrahydrafuran (THF) were added by syringe as solvents. This solution was allowed to cool to -78° C. in an ethanol/dry ice bath for 15 minutes while stirring. After it was cool, 13.8 mL (0.0343 mol) n-butyl lithium were added slowly via syringe and the solution was kept at -78° C. for 30 minutes. It was then allowed to warm to room temperature for 30 minutes, and consequently placed in an ice water bath for one hour. It was then again cooled to -78° C. To a separate round bottom flask, 2.60 mL (0.312 mol) 2-Furaldehyde were added via syringe and 30 mL of anhydrous ether were added. This solution was cooled to -78° C. The furaldehyde solution was added to the furan solution dropwise by canula. The reaction was kept at -78° C. for two hours, and then it was allowed to slowly warm to room temperature overnight.

The lithium salt was quenched with 10% $NH_4Cl$ solution, a white precipitate formed immediately, and then disappeared after the reaction mixture had stirred for 10 minutes. The aqueous layer was separated from the organic layer and was extracted three times with ether. The organic layers were combined, dried with $MgSO_4$ and the solvent was evaporated by rotary evaporation. A proton NMR was taken of this yellowish oil in $CDCl_3$ which revealed the desired alcohol had been formed. Synthesis of 2-furyl-2'-thienyl methanol. 50.00 mL (0.6244 mol) of thiophene were placed in a round bottom flask and 20.0 mL of anhydrous THF and 20.0 mL anhydrous ether were added via syringe. The solution was stirred and cooled to -78° C. 13.75 mL (0.03434 mol) nButyllithium were then added by syringe and the reaction was allowed to proceed for 30 minutes at this temp. It was then allowed to warm slowly to room temperature for 30 minutes, and placed in an ice bath for 60 minutes. It was again cooled to -78° C. In a separate flask, 2.60 mL (0.3122 mol) 2-Furaldehyde were added via syringe and 30 mL anhydrous ether was added as well; this solution was cooled to -78° C. The furaldehyde solution was then added to the thiophene solution dropwise via canula. The reaction was kept at -78° C. for 2 hours and then was allowed to slowly warm to room temperature overnight. 10% $NH_4Cl$ was added to quench the Lithium salt, and the aqueous layer was separated and extracted three times with ether. The organic layers were combined, dried with $MgSO_4$ and the solvents were removed by rotary evaporation. The proton NMR spectra revealed the alcohol had been produced. Synthesis of 2-Furylphenyl photochrome. 4.31 mL (0.0520 mol) of 2-Furaldehyde were placed in a round bottom flask via syringe, and 15 mL of anhydrous THF were added via syringe. The solution was cooled to -78° C. 52.0 mL (0.156 mol) of Phenylmagnesium bromide (3.0 M in anhydrous ether) were added via syringe and the reaction was kept at −78° C. for two hours and then it was allowed to slowly warm to room temperature overnight. A white precipitate was found in the flask. 10% $NH_4Cl$ was added to the flask in order to quench the lithium salt. A white precipitate was found in the aqueous layer, it was filtered off and set aside. The liquid phases were then separated, and the aqueous phase was extracted three times with ether. The organic layers were combined and dried with $MgSO_4$ before the solvent was removed by rotary evaporation. 5.35 g (0.0307 mol) of this product (assumed to be 2-Furylphenyl methanol) were placed in a reaction flask and 100 mL of non-anhydrous benzene were added. The alcohol was allowed to dissolve and 4.8652 g (0.0214 mol) of 2,3-Dichloro-5,6-dicyanobenzoquinone (DDQ) were added. This reaction was allowed to stir for 10 days. After 10 days, the TLC on silica gel showed that most of the product had reacted. The DDQ solid was filtered off and the filtrate was rotovapped down onto silica gel. A flash chromatography column was run on half of the silica gel using 80% Hexane/ 20% Ether as an eluent. Fractions 10 through 15 were combined and were determined to be the desired ketone by proton NMR analysis. 0.508 g (0.00337 mol) of the ketone were placed in a round bottom flask and 10.2 mL anhydrous THF were added via syringe. 22.5 mL (0.00757 mol) of Ethynylmagnesium bromide (0.5 M in anhydrous THF) were added to the flask by syringe and the reaction was allowed to stir for 7 days. TLC was performed on the reaction, indicating the reaction had come to completion. 10% $NH_4Cl$ was added to the flask and the aqueous layer was then separated and extracted three times with ether. The organic layers were combined, dried with $MgSO_4$ and rotovapped down. A proton NMR of the product revealed the product had been received. 0.220 g ($6.91 \times 10^{-4}$ mol) of the propargyl alcohol were placed in a round bottom flask and 20 mL of non-anhydrous benzene were added. 0.0030 g ($6.91 \times 10^{-6}$ mol) of PTSA were added as a catalyst as well as 0.1200 g ($8.323 \times 10^{-4}$ mol) of 2-Napthol. This reaction was allowed to stir overnight. This reaction was monitored by TLC, and when ultraviolet radiation was applied to the silica gel plate, the photochromic compound turned orange. (NOTE: This is how far I am on this reaction.) Synthesis of 2-Thienylphenyl photochrome. 2.0201 g (0.010624 mol) of 2-Benzoylthiophene were placed in a round bottom flask and 20.00 mL anhydrous THF were added via syringe, and the reactant was allowed to dissolve. 32.0 mL (0.0159 mol) Ethynylmagnesium bromide were added via syringe, and the reaction was allowed to proceed for 5 days, until the reaction was thought to be complete by TLC. 10% $NH_4Cl$ was added to the reaction vessel and the aqueous layer was then separated and extracted three times with ether. The aqueous layers were combined, dried with $MgSO_4$ and the solvent was removed by rotary evaporation. A proton NMR revealed the propargyl alcohol had been formed. 2.37 g (0.0111 mol) of the propargyl alcohol were placed in a round bottom flask and 60 mL of non-anhydrous benzene were added. 1.5934 g (0.0111 mol) of 2-Napthol were added, as well as 0.0222 g (0.000117 mol) PTSA as a catalyst. The reaction was allowed to stir overnight. The reaction was monitored by TLC. Upon its completion, 15% NaOH was added to the flask. The aqueous layer was separated and extracted three times with ether. The organic layers were combined and dried with $MgSO_4$ before the solvents were removed by rotary evaporation. A proton NMR revealed the product had been formed. The product was rotovapped onto silica gel and a flash column chromatography was performed, using 95% Hexane/5% Ethyl Acetate as the eluent. In fractions 8 and 9, white, fluffy crystals came out of solution. They were filtered off and the filtrate was combined with fractions 5 through 7. The solvents were rotovapped off and light peach colored crystals were obtained. Synthesis of 2-Thiophenyl ortho-methoxyphenyl photochrome. 2.0167 g (0.0092395 mol) of 2-(4-Methoxybenzoyl)-thiophene were placed in a round bottom flask and 20.00 mL anhydrous THF were added via syringe. The reactant was allowed to dissolve, and then 27.5 mL (0.0137 mol) Ethynylmagnesium bromide were added via syringe. The reaction was monitored by TLC. It was allowed to react for 5 days. 10% $NH_4Cl$ was then added to the flask and the aqueous layer was separated and extracted three times with ether. The organic layers were combined and dried with $MgSO_4$ before the solvents were removed by rotary evaporation. A proton NMR revealed the propargyl alcohol had been produced. 2.13 g (0.00872 mol) of the propargyl alcohol were placed in a round bottom flask and 60 mL of non-anhydrous benzene were added. 1.2571 g (0.00872 mol) 2-Napthol were added, as well as 0.0210 g ($1.10 \times 10^{-4}$ mol) of PTSA as a catalyst. The reaction was monitored by TLC and was allowed to stir for 5 days. 15% NaOH was added to the flask and the aqueous layer was removed and extracted three times with ether. The organic layers were then recombined and dried with $MgSO_4$; the solvents were removed by rotary evaporation. The proton NMR of this product revealed the desired product had been synthesized and it was relatively pure. The product was then re-rotovapped down onto silica gel. Flash column chromatography was performed on the silica gel using 95% Hexane/ 5% Ethyl Acetate as the solvent. The product was present in fractions 4 through 20. The product was obtained by evaporating the solvent. Synthesis of (5'Carboxy)-2-thienlphenyl photochrome. 0.2072 g ($6.086 \times 10^{-4}$ mol) of 2-thienylphenyl were placed in a round bottom flask and 10 mL anhydrous THF and 10 mL anhydrous ether were added via syringe. The solution was stirred and cooled to −78° C. 0.3 mL ($6.695 \times 10^{-4}$ mol) n-butyl lithium were added via syringe, and the reaction was allowed to stir for an hour. In a separate round bottom flask, dry ice was added. The solid carbon dioxide was allowed to sublime in the closed container, and then the $CO_2$ gas was added to the solution of the first flask by canula. The $CO_2$ was allowed to enter the flask for 105 minutes at room temperature. The reaction was then allowed to stir for a week. 15% NaOH was added three times to extract the ionic species from the organic solvents. The aqueous phases were combined and concentrated HCl was then added dropwise to the reaction vessel until universal indicator paper showed the solution was strongly acidic. Precipitate was formed, and this was filtered off by vacuum filtration. Pure product also formed in the filtrate solution, this was also filtered to retrieve it. A proton NMR spectra revealed the product had been formed. When the product was placed in basic water, the solution was slightly yellow; upon addition of ultraviolet light, the solution turned pink.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. An ionic photochromic compound, comprising:
   (a) a pyran moiety comprising oxygen as a ring constituent;
   (b) an aromatic moiety comprising an aromatic ring fused to the pyran moiety;
   (c) at least one heterocyclic ring moiety linked to the pyran moiety at an ortho position relative to the oxygen ring constituent; and
   (d) at least one carboxylate moiety linked to the heterocyclic ring moiety.

2. The ionic photochromic compound of claim 1, wherein the aromatic ring fused to the pyran moiety comprises a phenyl moiety.

3. The ionic photochromic compound of claim 1, wherein the aromatic ring fused to the pyran moiety comprises a substituted phenyl moiety.

4. The ionic photochromic compound of claim 3, wherein the substituted phenyl moiety comprises —NO$_2$ as a substituent.

5. The ionic photochromic compound of claim 3, wherein the substituted phenyl moiety has the formula:

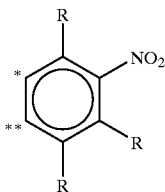

wherein the carbon atoms of the ring denoted with the "*" and "" symbols are the carbon atoms which are fused to the pyran moiety in a manner such that the carbon atom denoted with the "" symbol is ortho to the oxygen atom of the pyran ring, and each R is independently a monovalent moiety or a co-member of a ring structure with another R group.

6. The ionic photochromic compound of claim 1, wherein the aromatic moiety fused to the pyran moiety comprises a naphthyl moiety.

7. The ionic photochromic compound of claim 6, wherein the naphthyl moiety has the formula:

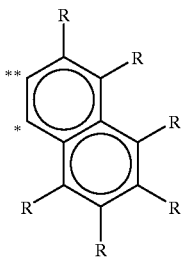

wherein the carbon atoms denoted with the "*" and "" symbols are the carbon atoms which are fused to the pyran moiety in a manner such that the carbon atom denoted with the "" symbol is ortho to the oxygen atom of the pyran ring, and each R is independently a monovalent moiety or a co-member of a ring structure with another R group.

8. The ionic photochromic compound of claim 1, wherein the aromatic moiety fused to the pyran moiety has a formula selected from:

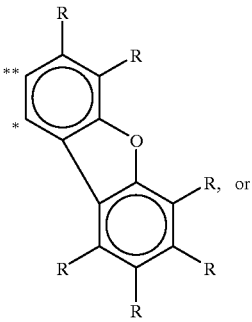

-continued

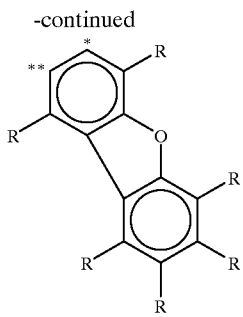

wherein the carbon atoms of each moiety denoted with the "*" and "" symbols are the carbon atoms which are fused to the pyran moiety in a manner such that the carbon atom denoted with the "" symbol is ortho to the oxygen atom of the pyran ring, and each R is independently a monovalent moiety or a co-member of a ring structure with another R group.

9. The ionic photochromic compound of claim 1, wherein the photochromic compound further comprises an aromatic moiety comprising an aromatic ring which is fused to the heterocyclic ring moiety.

10. The ionic photochromic compound of claim 9, wherein the aromatic moiety fused to the heterocyclic ring moiety comprises a phenyl moiety.

11. The ionic photochromic compound of claim 9, wherein the aromatic moiety fused to the heterocyclic ring comprises an unsubstituted phenyl moiety.

12. The ionic photochromic compound of claim 1, wherein the heterocyclic ring moiety has the formula:

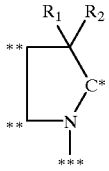

wherein the carbon atom denoted by the symbol "*" is also the carbon atom of the pyran moiety which is at an ortho position relative to the oxygen atom of the pyran moiety such that said ortho carbon atom is a ring member of both the pyran moiety and the heterocyclic ring moiety; the carbon atoms denoted by the symbol "" are fused to an aromatic ring; the single bond denoted by the "*" symbol is linked to the carboxylate moiety by a divalent linking group; and each of R$_1$ and R$_2$ is independently a monovalent moiety other than H or an acidic group or are co-members of a cyclic ring structure.

13. The ionic photochromic compound of claim 12, wherein R$_1$ and R$_2$ are each independently a lower alkyl group of 1 to 4 carbon atoms.

14. The ionic photochromic compound of claim 1, wherein the heterocyclic ring moiety comprises a thiophenyl moiety.

15. The ionic photochromic compound of claim 1, wherein the heterocyclic ring moiety has the formula:

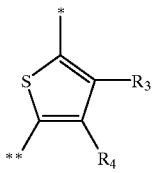

wherein the single bond denoted with the "*" symbol is linked to the ortho carbon of the pyran moiety; the single bond denoted by the "**" symbol is linked to the carboxylate moiety; and $R_3$ and $R_4$ are each independently a monovalent moiety or, in combination, co-members of a ring structure fused to the thiophenyl ring.

16. The ionic photochromic compound of claim 1, further comprising a divalent linking group linking the carboxylate moiety to the heterocyclic ring moiety.

17. The ionic photochromic compound of claim 16, wherein the divalent linking group comprises 4 to 20 carbon atoms.

18. The ionic photochromic compound of claim 16, wherein the divalent linking group comprises 4 to 10 carbon atoms.

19. The ionic photochromic compound of claim 16, wherein the divalent linking group comprises a moiety of the formula:

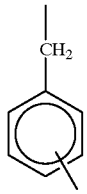

wherein the valent sites of the aromatic ring of said divalent group that are not used to link the carboxylate moiety to the heterocyclic ring moiety each comprise a monovalent substituent or are members of a cyclic ring structure substituent.

20. The ionic photochromic compound of claim 1, wherein the photochromic compound has the formula:

$$A_1-P_{o,c}-H_C-X-COO^{\ominus}M^{\oplus}$$

wherein $P_{o,c}$ is the pyran moiety which may exist in an open configuration, $P_o$, or a closed configuration, $P_c$; $A_1$ is the aromatic moiety comprising an aromatic ring fused to the pyran moiety; $H_c$ is a moiety comprising the heterocyclic ring moiety linked to the saturated carbon atom of the pyran moiety which is at the ortho position relative to the oxygen ring constituent of the pyran moiety; X is a single bond or a divalent linking group connecting the carboxylate moiety to the heterocyclic ring moiety; and $M^{\oplus}$ is a monovalent counter cation selected from $H^+$, $Na^+$, $Li^+$, K, $NH_4^+$, $H-NR_3^{\oplus}$, and combinations thereof, wherein each R is a monovalent substituent other than hydrogen or an acid group.

21. The ionic photochromic compound of claim 1, wherein the photochromic compound has the formula:

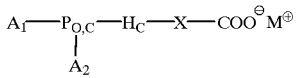

wherein $P_{o,c}$ is the pyran moiety which may exist in an open configuration, $P_o$, or a closed configuration, $P_c$; $A_1$ is the aromatic moiety comprising an aromatic ring fused to the pyran; $H_c$ is a moiety comprising the heterocyclic ring moiety linked to the saturated carbon atom of the pyran moiety which is at the ortho position relative to the oxygen ring constituent of the pyran moiety; $A_2$ is selected from an aromatic moiety, a heterocyclic moiety; an aromatic heterocyclic moiety, said moiety being linked to the saturated carbon atom of the pyran moiety which is at an ortho position relative to the oxygen ring constituent of the pyran moiety; X is a single bond or a divalent linking group connecting the carboxylate moiety to the heterocyclic ring moiety; and $M^{\oplus}$ is a monovalent counter cation selected from $H^+$, $Na^+$, $Li^+$, $K^+$, $NH_4^+$, $H-NR_3^{\oplus}$, and combinations thereof, wherein each R is a monovalent substituent other than hydrogen or an acid group.

22. The ionic photochromic compound of claim 1, wherein the photochromic compound has the formula:

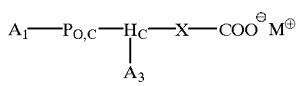

wherein $P_{o,c}$ is the pyran moiety, $A_1$ is the aromatic moiety comprising an aromatic ring fused to the pyran, $H_c$ is the heterocyclic ring moiety linked to the saturated carbon atom of the pyran moiety which is at the ortho position relative to the oxygen ring constituent of the pyran moiety, $A_3$ is an aromatic moiety comprising an aromatic ring fused to the heterocyclic ring moiety, X is a single bond or a divalent linking group connecting the carboxylate moiety to the heterocyclic ring moiety, and $M^{\oplus}$ is a monovalent counter cation selected from $H^+$, $Na^+$, $Li^+$, $K^+$, $NH_4^+$, $H-NR_3^{\oplus}$, and combinations thereof, wherein each R is a monovalent substituent other than hydrogen or an acid group.

23. The ionic photochromic compound of claim 1, wherein the photochromic compound has the formula:

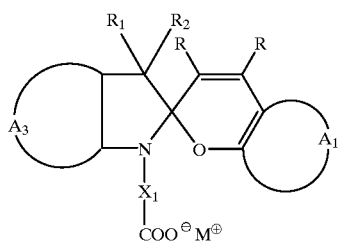

wherein $A_1$ is the aromatic moiety comprising the aromatic ring fused to the pyran moiety; $R_1$ and $R_2$ are each independently a monovalent moiety other than H or an acidic moiety or are co-members of a cyclic ring structure; each R is independently a monovalent substituent or, in combination with the other R, a co-member of a ring structure; $A_3$ is an aromatic moiety comprising an aromatic ring fused to the heterocyclic ring moiety containing the nitrogen atom; $X_1$ is a divalent linking group; and $M^{\oplus}$ is a cationic counterion selected from $H^+$, $Na^+$, $Li^+$, $K^+$, $NH_4^+$, $H-NR_3^{\oplus}$, and combinations thereof, wherein each R' is a monovalent substituent other than hydrogen or an acid group.

24. The ionic photochromic compound of claim 23, wherein $A_1$ is selected from the group consisting of

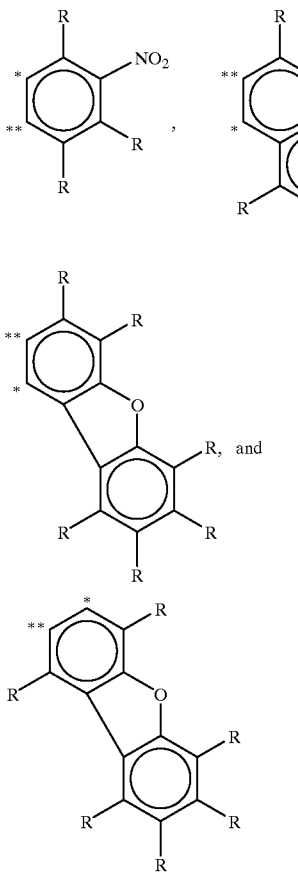

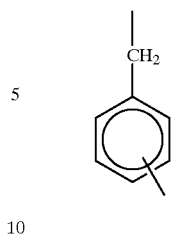

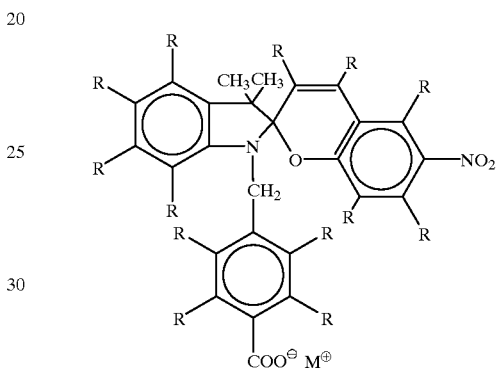

wherein the valent sites of the aromatic ring of said divalent group that are not used to link the carboxylate moiety to the heterocyclic ring moiety each comprise a monovalent substituent or are members of a cyclic ring structure substituent.

27. The ionic photochromic compound of claim 1, wherein the photochromic compound has the formula:

wherein the substituents of the compound other than the —$CH_3$, —$COO^{\ominus}M^{\oplus}$, and —$NO_2$ moieties are hydrogen.

28. The ionic photochromic compound of claim 1, wherein the photochromic compound has the formula:

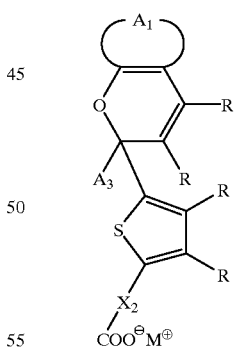

wherein the carbon atoms of each moiety denoted with the "*" and "" symbols are the carbon atoms which are fused to the pyran moiety in a manner such that the carbon atom denoted with the "" symbol is ortho to the oxygen atom of the pyran ring, and each R is independently a monovalent moiety or a co-member of a ring structure with another R group.

25. The ionic photochromic compound of claim 23, wherein $A_3$ has the formula:

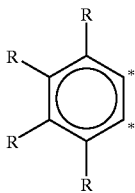

wherein the carbon atoms denoted with the "*" symbol are the carbon atoms which are fused to the heterocyclic ring moiety, and each R is independently a monovalent moiety or a co-member of a cyclic ring structure with another R group.

26. The ionic photochromic compound of claim 23, wherein $X_1$ has the formula:

wherein $A_1$ is an aromatic moiety comprising an aromatic ring fused to the pyran moiety; each R is each independently a monovalent moiety or, in combination with another R, a co-member of a cyclic ring structure; $A_3$ is a monovalent aromatic, heterocyclic, or aromatic heterocyclic moiety; and $X_2$ is a single bond or a divalent linking group.

29. The ionic photochromic compound of claim 28, wherein $A_1$ has the formula:

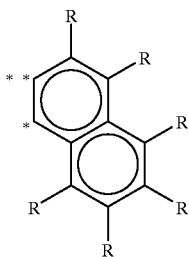

wherein the carbon atoms denoted with the "*" and "" symbols are the carbon atoms which are fused to the pyran moiety in a manner such that the carbon atom denoted with the "" symbol is ortho to the oxygen atom of the pyran ring, and each R is independently a monovalent moiety or a co-member of a ring structure with another R group.

30. The ionic photochromic compound of claim 28, wherein each R attached to the pyran ring is independently selected from a lower alkyl group of 1 to 4 carbon atoms.

31. The ionic photochromic compound of claim 28, wherein $X_2$ is a single bond.

32. The ionic photochromic compound of claim 28, wherein $A_3$ comprises a phenyl moiety.

33. The ionic photochromic compound of claim 28, wherein the photochromic compound has the formula:

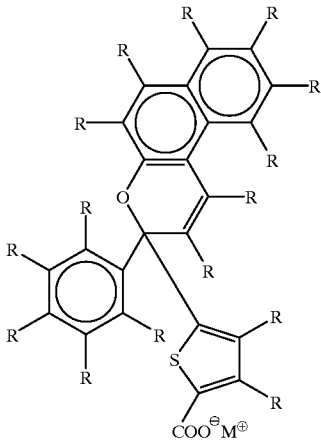

wherein each R is hydrogen.

34. A method of making an ionic photochromic compound, comprising the steps of:
(a) providing a reactant comprising a heterocyclic ring including a nitrogen atom as a ring constituent and comprising an aromatic moiety having an aromatic ring fused to the heterocyclic ring;
(b) attaching a carboxyl moiety to the nitrogen atom in a manner such that the carboxyl moiety is linked to the nitrogen atom by a divalent linking group;
(c) providing an aromatic reactant comprising an aromatic ring having substituents reactive with the product of step (b) to form a reaction product comprising a pyran ring having an oxygen atom as a ring substituent and a saturated carbon atom ortho to the oxygen atom, said substituents being reactive such that the aromatic ring of the aromatic ring is fused to the resultant pyran ring and the saturated carbon atom of the pyran ring ortho to the oxygen atom is linked to the heterocyclic ring; and
(d) reacting the product of step (b) with the aromatic reactant under conditions effective to form said pyran ring, whereby the ionic photochromic compound is formed.

35. The method of claim 34, wherein the reactant of step (a) has the formula

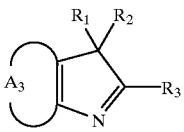

wherein each of $R_1$ and $R_2$ is independently a monovalent moiety other than H or an acidic group or $R_1$ and $R_2$ are co-members of a cyclic ring structure; $R_3$ is

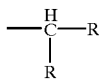

wherein each R is independently a monovalent substituent; and $A_3$ is an aromatic moiety comprising an aromatic ring fused to the heterocyclic ring.

36. The method of claim 34, wherein the reactant of step (a) has the formula:

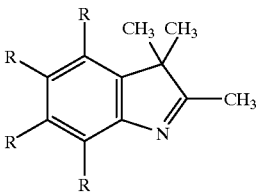

wherein each R is hydrogen.

37. The method of claim 34, wherein step (b) comprises reacting the reactant of step (a) with a carboxyl functional compound having the formula:

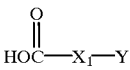

wherein $X_1$ is a divalent linking group and Y is selected from the group consisting of a halogen atom and a tosylate group.

38. The method of claim 35, wherein step (b) comprises reacting a carboxyl functional compound with the reactant of step (a) according to the following reaction scheme

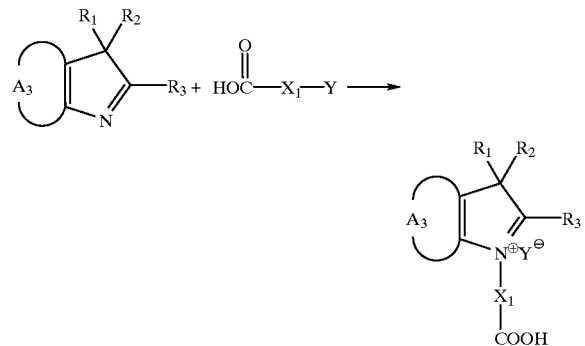

wherein $X_1$ is a divalent linking group; and Y is selected from the group consisting of a halogen atom and a tosylate group.

39. The method of claim 38, wherein $X_1$ is

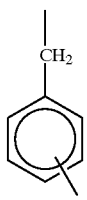

wherein the valent sites of the aromatic ring of said divalent group that are not used to link the carboxylate moiety to the heterocyclic ring moiety each comprise a monovalent substituent or are members of a cyclic ring structure substituent.

40. The method of claim 38, wherein Y is bromine.

41. The method of claim 34, wherein the aromatic reactant of step (c) has the formula

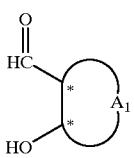

wherein $A_1$ is an aromatic moiety comprising an aromatic ring; and the carbon atoms denoted with the "*" symbols are constituents of said aromatic ring.

42. The method of claim 34, wherein the aromatic reactant of step (c) has the formula:

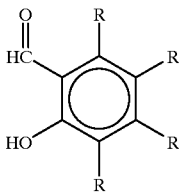

wherein each R is independently a monovalent moiety or a co-member of a cyclic ring structure with another R.

43. The method of claim 42, wherein step (c) is carried out under basic conditions in a solvent comprising an alcohol.

44. The method of claim 43, wherein the alcohol is ethanol.

45. The method of claim 43, wherein the solvent further comprises at least two equivalents of a base per equivalent of the carboxyl functional reaction product of step (b).

46. A method of making a photochromic compound, comprising the steps of:

(a) providing a first reactant of the formula:

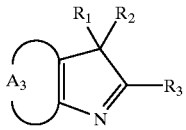

wherein each of $R_1$ and $R_2$ is independently a monovalent moiety other than H or an acidic group or $R_1$ and $R_2$ are co-members of a cyclic ring structure; $R_3$ is —$CH_3$; and $A_3$ is an aromatic moiety comprising an aromatic ring fused to the heterocyclic ring.

(b) providing a second reactant of the formula:

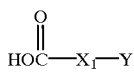

wherein $X_1$ is a divalent linking group and Y is selected from the group consisting of a halogen atom and a tosylate group;

(c) reacting the first reactant with the second reactant according to the following reaction scheme:

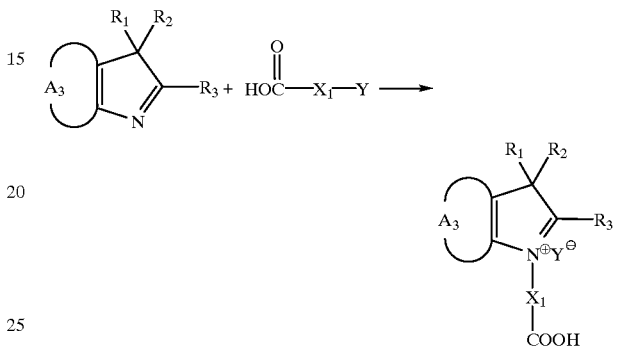

(d) providing a third reactant of the formula:

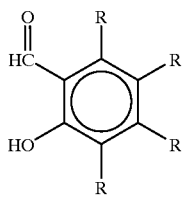

wherein each R independently is a monovalent moiety or, in combination with another R substituent, is a co-member of a cyclic ring structure; and (e) reacting the product of step (c) with the third reactant according to the following reaction scheme:

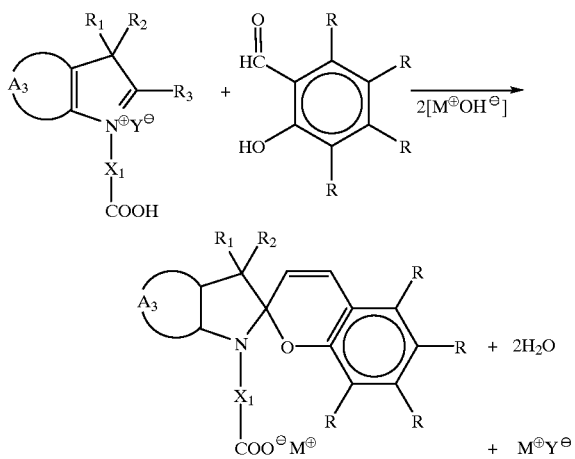

whereby the photochromic compound is formed.

47. The method of claim 46, wherein the Y is bromine.

48. The method of claim 46, wherein at least one R is —$NO_2$.

49. The method of claim 46, wherein step (c) is carried out under basic conditions in a solvent comprising an alcohol.

50. The method of claim 49, wherein the alcohol is ethanol.

51. A method of making a photochromic compound, comprising the steps of:

(a) providing a first reactant of the formula:

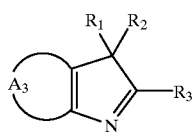

wherein each of $R_1$ and $R_2$ is independently a monovalent moiety other than H or an acidic group or $R_1$ and $R_2$ are co-members of a cyclic ring structure; $R_3$ is —$CH_3$; and $A_3$ is an aromatic moiety comprising an aromatic ring fused to the heterocyclic ring;

(b) providing a second reactant of the formula:

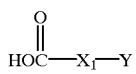

wherein $X_1$ is a divalent linking group and Y is selected from the group consisting of a halogen atom and a tosylate group;

(c) reacting the first reactant with the second reactant according to the following reaction scheme:

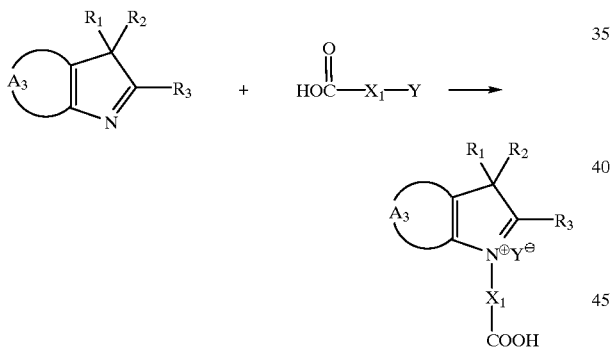

(d) providing a third reactant of the formula:

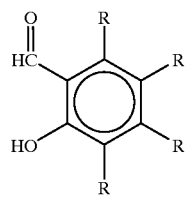

wherein each R independently is a monovalent moiety or, in combination with another R substituent, is a co-member of a cyclic ring structure; and (e) reacting the product of step (c) with the third reactant according to the following reaction scheme:

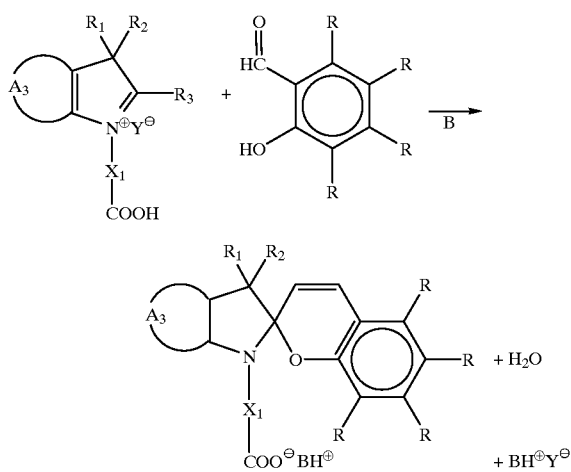

whereby the photochromic compound is formed.

* * * * *